United States Patent [19]

Schwartz et al.

[11] Patent Number: 5,300,249
[45] Date of Patent: * Apr. 5, 1994

[54] MILD PERSONAL CLEANSING BAR COMPOSITION WITH BALANCED SURFACTANTS, FATTY ACIDS, AND PARAFFIN WAX

[75] Inventors: James R. Schwartz; Richard D. Farris, both of West Chester; Theresa A. Bakken, Cincinnati; Lawrence A. Gilbert, West Chester; Wayne E. Eccard, Cleves; James C. Dunbar, Cincinnati, all of Ohio

[73] Assignee: The Procter & Gamble Company, Cincinnati, Ohio

[*] Notice: The portion of the term of this patent subsequent to Oct. 13, 2009 has been disclaimed.

[21] Appl. No.: 763,794

[22] Filed: Sep. 23, 1991

[51] Int. Cl.$^5$ ................................. C11D 9/00
[52] U.S. Cl. .................... 252/108; 252/121; 252/550; 252/DIG. 3; 252/DIG. 16
[58] Field of Search .............. 252/108, 121, 132, 550, 252/DIG. 5, DIG. 16

[56] References Cited

U.S. PATENT DOCUMENTS

| | | | |
|---|---|---|---|
| 2,653,913 | 9/1953 | van Dijck et al. | 252/161 |
| 2,734,870 | 2/1956 | Lewis | 252/161 |
| 2,988,511 | 6/1961 | Mills et al. | 252/121 |
| 3,129,187 | 4/1964 | Meehan | 252/155 |
| 3,940,220 | 2/1976 | D'Arcangeli | 425/131.1 |
| 4,151,105 | 4/1979 | O'Roark | 252/145 |
| 4,335,025 | 6/1982 | Barker et al. | 252/550 |
| 4,515,721 | 5/1985 | Login et al. | 260/400 |
| 4,673,525 | 6/1987 | Small et al. | 252/132 |
| 4,812,253 | 3/1989 | Small et al. | 252/132 |
| 5,041,233 | 8/1991 | Kutny et al. | 252/121 |
| 5,064,555 | 11/1991 | Medcalf, Jr. et al. | 252/117 |
| 5,084,212 | 1/1992 | Farris et al. | 252/554 |
| 5,096,608 | 3/1992 | Small et al. | 252/132 |
| 5,132,037 | 7/1992 | Greene et al. | 252/108 |
| 5,154,849 | 10/1992 | Visscher et al. | 252/174.15 |
| 5,186,855 | 2/1993 | Crudden | 252/117 |

FOREIGN PATENT DOCUMENTS 3442579A 5/1986 Fed. Rep. of Germany.
3616843A 11/1987 Fed. Rep. of Germany.

*Primary Examiner*—Gary P. Strabb
*Assistant Examiner*—Timothy C. Vanoy
*Attorney, Agent, or Firm*—Leonard Williamson

[57] ABSTRACT

This invention is an improved mild personal cleansing syndet bar comprising: long chain synthetic surfactant having essentially saturated $C_{15}$–$C_{22}$, preferably $C_{16}$–$C_{18}$, alkyl or acyl chains, more preferably cetearyl sulfate; a high lathering, mild synthetic surfactant, preferably $C_{12}$–$C_{14}$ acyl isethionate; soap; fatty acids; sodium isethionate; and paraffin wax, preferably a high melting point paraffin wax. The bar has improved processability, good smears, and good in-use properties without meaningful lather negatives.

13 Claims, No Drawings

MILD PERSONAL CLEANSING BAR COMPOSITION WITH BALANCED SURFACTANTS, FATTY ACIDS, AND PARAFFIN WAX

TECHNICAL FIELD

This invention relates to personal cleansing bars based on synthetic surfactants and to processes of making them.

BACKGROUND OF THE INVENTION

"Soap, since its appearance in history, has helped safeguard two of our greatest treasures: our health and our children. Health is directly related to cleanliness. Data proves that the higher the consumption of soap in a country, the lower will be the infant mortality rate.

"In industralized countries, soap is the most-taken-for-granted and readily available personal care product used on our body daily. Soap is also the most inexpensive product we use in relation to its per use cost. In many less fortunate countries both laundry and toilet soaps are still scarce, expensive essentials . . . .

"Soap is most probably the oldest of toiletries, and, in spite of being readily available in most parts of the world, it is still scarce in many countries. The oldest literary reference to soap relates to the washing of wool and is found in clay Sumarian tablets dating about 2500 B.C.E. Sumerian was a language spoken in the area of the Tigris and Euphrates Rivers, now Southern Iraq. The patriarch Abraham and his family came from Sumer. Another Sumerian tablet, dating 2200 B.C.E. gives the formula consisting of water, alkali and cassia oil.

"Cleanliness is essential to our well being. A clean body, clean bath, clean home, and clean environment are the norm today." (Soap Technology for the 1990's, L. Spitz et al., American Oil Chemists' Society, Champaign, Ill., pp. 1-2) This reference discusses syndet and combo bars, particularly on pp. 209-229.

Synthetic surfactant-based personal cleansing bars have attracted much interest recently because they can be selected to be milder to the skin than soap-based products. This mildness, however, comes with negatives to both the manufacturer and the consumer. The bar soap manufacturer experiences difficult processability due to the sticky nature of such products, as well as high raw material costs. The consumer experiences the negative performance properties of poor lather, messy smear, bar softness, and consequently, high wear rates.

U.S. Pat. No. 2,988,511, Mills and Korpi, issued Jun. 13, 1961, incorporated herein by reference, discloses a milled detergent bar with at least 75% by weight of: (1) 15%–55% of anionic sulfuric reaction products which do not hydrolyze unduly, said salts being selected from sodium and potassium salts, and said anionic organic sulfuric reaction products containing at least 50% alkyl glyceryl ether sulfonates, 10%–30% of which are alkyl diglyceryl ether sulfonates, the alkyl radicals containing 10–20 carbon atoms; (2) 5%–50% soap; and (3) 20%–70% of a binder material selected from freshly precipitated calcium soaps of fatty acids having 10–18 carbon atoms, freshly precipitated magnesium soap, starch, normally solid waxy materials which will become plastic under conditions encountered in the milling of soap. Paraffin is not mentioned in Mills et al. '511.

Commonly assigned U.S. Pat. No. 4,673,525, Small et al., issued Jun. 16, 1987, discloses mild personal cleansing bars based on selected mild surfactant; moisturizer; 0%–5% polymeric skin mildness aid; and some soap. This patent goes a long way in providing a practical mild personal cleansing bar; but some processing problems have been experienced due to the sticky nature of some of the preferred ingredients.

The use of paraffin wax in synthetic surfactant-based bars, per se, is known. However, the known bars suffer from a combination of harshness and/or lather deficiencies. E.g., U.S. Pat. No. 2,653,913, van Dijck et al., issued Sep. 29, 1953, discloses bars comprising 80% synthetic anionic surfactant (selected from sodium secondary or primary alkyl sulfates or sodium dodecylbenzene sulfonate), 18% paraffin, melting point (M.P.) 140°–150° F., and 2% sodium alginate. The surfactants employed are non-mild surfactants.

U.S. Pat. No. 2,734,870, Lewis, issued Feb. 14, 1956, discloses bars comprising 40–60% paraffin (M.P.>125° F.), 2–5% fatty acid, and 60–40% sodium alkyl aryl sulfonate. The high level of paraffin in these bars results in unacceptably low lather.

U.S. Pat. No. 3,129,187, Meehan, issued Apr. 14, 1964, discloses bars comprising 50–75% sodium alkylbenzene sulfonate, 5–35% stearyl alcohol, 1–25% paraffin (M.P. 125°–170° F.), and 2–25% stearyl MEA. The harsh surfactants employed would result in harsh products.

U.S. Pat. No. 4,151,105, O'Roark, issued Apr. 24, 1979, discloses bars comprising 20–40% synthetic anionic surfactant (composed of sodium cocoyl isethionate and/or sodium lauryl sulfoacetate), 10–30% paraffin (M.P. 130°–140° F.), 5–15% powdered starch, 10–30% dextrin and 5% fatty acid. The low melting point of the wax employed would cause a substantial soil load on the lather potential and result in poor lather volumes. The synbars of the present invention are preferably free of dextrin and powdered starch.

U.S. Pat. No. 4,335,025, Barker et al., issued Jun. 15, 1982, discloses a process for making syndet bars containing a "waxy extender."

OBJECTS OF THE INVENTION

One object of this invention is to provide a personal cleansing syndet bar composition which exhibits improved processability of the syndet bar while not sacrificing lather or bar messiness.

SUMMARY OF THE INVENTION

This invention relates to an improved processable, mild personal cleansing syndet bar comprising: long chain $C_{15}$–$C_{22}$ alkyl or acyl synthetic surfactant having essentially saturated, preferably $C_{16}$–$C_{18}$, alkyl chains, soap, free fatty acid, a lathering mild surfactant comprising $C_{12}$–$C_{14}$ alkyl (cocoyl) isethionate, and a selected paraffin wax. The bar has improved procssability without a meaningful bar messiness or lather negative. More specifically the composition comprises:

A. from about 4% to about 32% of essentially saturated long chain ($C_{15}$–$C_{22}$ alkyl) synthetic surfactant selected from the group consisting of: alkyl sulfate, acyl isethionate, alkyl sarcosinate, alkyl glyceryl ether sulfonate, and mixtures thereof;

B. from about 4% to about 30% of paraffin wax having a melting point of from about 130° F./54° C. to about 180° F./82° C;

C. from about 20% to about 70% lathering mild synthetic surfactant; and wherein said lathering mild synthetic surfactant is selected from $C_{12}$–$C_{14}$ acyl isethionate, $C_{12}-C_{14}$ alkyl glyceryl ether sulfonate, $C_{12}-C_{14}$ sodium acyl sarcosinate, and mixtures thereof; and wherein at least about 10% of said bar is said mild lathering $C_{12}-C_{14}$ alkyl isethionate;

D. from about 2% to about 30% free fatty acid;
E. from 0% to about 15%, preferably from about 2% to about 10%, soap;
F. from about 2% to about 8% sodium isethionate;
G. from 0% to about 2% sodium chloride; and
H. from about 1.5% to about 10% water;

wherein said bar has a pH of from about 4.0 to about 9.0.

When the level of $C_{12}-C_{14}$ mild surfactant is from about 40% to about 70% by weight of the bar, the ratio of said stearic acid to said lauric acid is from about 5:1 to about 10:1.

When the level of $C_{12}-C_{14}$ mild surfactant is from about 30% to about 45%, the ratio of said stearic acid to said lauric acid is from about 2:1 to about 6:1.

When the level of $C_{12}-C_{14}$ mild surfactant is from about 20% to about 35%, the ratio of said stearic acid to said lauric acid is from about 0.1 to about 2:1.

DETAILED DESCRIPTION OF THE INVENTION

A mild synthetic surfactant-based (syndet) bar with improved processability, good lather and/or reduced messiness (smear) is indeed an advance in this art. The present invention provides such an improved syndet bar comprising: (1) from about 4% to about 32%, preferably from about 5% to about 30%, of $C_{15}-C_{22}$, preferably $C_{16}-C_{18}$, essentially saturated long chain alkyl sulfates; acyl isethionate, alkyl sarcosinate, alkyl glyceryl ether sulfonate, and mixtures thereof; (2) from about 20% to about 70%, preferably from about 30% to about 60% by weight of said bar, of mild, high lathering, synthetic surfactants with at least about 10% by weight of the bar being $C_{12}-C_{14}$ alkyl isethionate; (3) from about 2% to about 30%, preferably from about 3% to about 20%, of $C_{10}-C_{22}$, preferably $C_{12}-C_{18}$, essentially saturated fatty acids; (4) from 0% to about 15%, preferably from about 2% to about 10%, $C_{10}-C_{22}$, preferably $C_{12}-C_{18}$, alkali metal soaps, preferably sodium or potassium soaps; (5) from about 4% to about 30%, preferably from about 5% to about 28%, paraffin wax with an average melting point of from about 130° F. to about 180° F., preferably from about 140° F. to about 165° F., more preferably from about 142° F. to about 160° F.; (6) from 0% to about 10% auxiliary plastic binders such as polyethylene glycols and/or monoglyceride; (7) from about 1.5% to about 10%, preferably from about 2% to about 8%, more preferably from about 3% to about 6%, water; (8) from 0% to about 2% sodium chloride; and (9) from about 2% to about 8% sodium isethionate; and the pH of the bar is from 4 to 9, preferably from 5 to 8.

When the level of $C_{12}-C_{14}$ mild surfactant is from about 40% to about 70% by weight of the bar, the ratio of said stearic acid to said lauric acid is from about 5:1 to about 10:1.

When the level of $C_{12}-C_{14}$ mild surfactant is from about 30% to about 45%, the ratio of said stearic acid to said lauric acid is from about 2:1 to about 6:1.

When the level of $C_{12}-C_{14}$ mild surfactant is from about 20% to about 35%, the ratio of said stearic acid to said lauric acid is from about 0:1 to about 2:1.

While not being bound to any theory, it is advantageous to think of a synbar as comprising two separate components: the matrix and the actives. The matrix provides the physical characteristics (processability and bar messiness) while the actives provide lathering and mild properties. The matrix, if not chosen correctly, can impede lather generation, cause poor bar feel, increase or decrease wear rate beyond an acceptable level, and/or reduce product mildness. Likewise, the actives must be chosen so as to provide acceptable levels of lathering without negatively impacting mildness, a trade-off in formulations.

Bars with improved processability comprising long chain alkyl sulfate and selected binders are described in commonly assigned, copending U.S. patent applications: Ser. No. 07/605,614, J. R. Schwartz, W. E. Eccard, T. A. Bakken, and L. A. Gilbert, filed Oct. 30, 1990; Ser. No. 07/647,030, J. R. Schwartz, W. E. Eccard, T. A. Bakken, and L. A. Gilbert, filed Jan. 28, 1991; and Ser. No. 07/703,212, W. E. Eccard, J. R. Schwartz, T. A. Bakken, and L. A. Gilbert, filed May 20, 1991, all of said patent applications incorporated herein by reference. The present compositions yield bars having even better processability than those specifically exemplified in those patent applications.

The formulation of synthetic detergent-based (syndet) bars is a delicate balancing act. There are numerous bar use properties to take into consideration: lather, messiness, economy, product pH, bar firmness, etc. There are also numerous manufacturing aspects to balance: product stickiness, softness, ability to weld, and be transferred and stored conveniently. The present invention is of a personal cleansing bar which performs exceptionally well in all attributes (especially bar messiness) while having no negative processing issues.

It will be appreciated that the development of an appropriate bar matrix is a delicate balancing act between plasticity and brittleness while not comprising lather performance. Typical bar matrix plasticizer materials such as triglycerides, fatty alcohols, etc., which tend to form a sufficiently plastic matrix, but also tend to depress lather potential. Other commonly used additive matrix materials such as salts, polysaccharides, etc., tend to make an overly brittle and water-soluble matrix that induces poor bar messiness performance.

The terms "synthetic bar," also "syndet bar," as used herein mean that the "bar" has more synthetic surfactant than soap unless otherwise specified. The term "AS syndet bar" means a syndet bar containing alkyl sulfate surfactant or its equivalent, unless otherwise specified. The term "long chain" means $C_{15}$ and $C_{22}$, preferably $C_{16}-C_{20}$, and mixtures thereof. The terms "$C_{12}-C_{14}$ alkyl" and cocoyl" as used herein are synonymous.

The percentages, ratios, and parts herein are on a total composition weight basis, unless otherwise specified. All levels and ranges herein are approximations, unless otherwise specified. Levels of ingredients are expressed herein on a "solids" basis, incorporating all non-water components together, unless otherwise specified.

An essential element of the present invention is the surfactant system. The long chain alkyl sulfate (hereinafter including its long chain equivalent synthetic surfactants) is key and is defined herein, as comprising $C_{16}-C_{18}$ alkyl chains at a level of at least about 90%, preferably about 93%, and more preferably about 97%. The long chain alkyl sulfate (and its equivalents) is derived from corresponding saturated straight chain alcohols. The preferred alkyl sulfate has a ratio of $C_{16}-C_{18}$ alkyl chains in the range of from about 100% $C_{16}$ to about 100% $C_{18}$ by weight. A commercially available $C_{16}-C_{18}$ alkyl sulfate is SIPON® EC-111

(formerly SIPEX® EC-111), sodium cetearyl sulfate, which is approximately 60% $C_{16}$ and 36% $C_{18}$. SIPON® EC-111 is sold by Alcolac Company, Baltimore, Md. 21226. Another source is Henkel Corp., Ambler, Pa. 19002. Henkel's sodium cetearyl sulfate, LANETTE E, is an estimated 50–50% $C_{16}$–$C_{18}$ alkyl sulfate sold as an emulsifier.

Other long chain surfactants which are equivalents to the long chain alkyl sulfate (mostly insoluble) could serve as either full or partial replacements for the long chain alkyl sulfate. Examples includes long chain isethionates, sarcosinates, glyceryl ether sulfonates, etc. The acyl esters of isethionic acid salts, with esters of $C_{16}$–$C_{18}$ acyl isethionates and no more than 25% or lower $C_{14}$ acyl groups are also useful. Preferred is stearoyl isethionate with $C_{14}$ 3%; $C_{16}$ 50%; and $C_{18}$ 47%. Some preferred compositions include from about 3% to about 20% of stearoyl isethionate.

It is noted that surfactant mildness can be measured by a skin barrier destruction test which is used to access the irritancy potential of surfactants. In this test the milder the surfactant, the lesser the skin barrier is destroyed. Skin barrier destruction is measured by the relative amount of radio-labeled water ($^3H$—$H_2O$) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, Small et al., issued Jun. 16, 1987, incorporated herein by reference, and which disclose a mild alkyl glyceryl ether sulfonate (AGS) surfactant based synbar comprising a "standard" alkyl glyceryl ether sulfonate mixture. Barrier destruction testing surprisingly shows that the long chain alkyl sulfates are milder than standard AGS. The long chain alkyl sulfate preferably comprises 5–25% by weight of the bars of this invention.

The present invention contains a mild lathering surfactant at a level of from about 20% to about 70%, preferably from about 30% to about 60%. Examples of a high lathering or lather enhancing surfactant, especially milder ones, are: alkyl isethionate; sodium acyl sarcosinate, alkyl glyceryl ether sulfonate.

The isethionates, sarcosinates, and glyceryl ether sulfonates may be pure chain length variants or those derived from commercial oils such as coconut. The lauryl chain length should account for at least 20% to as much as 100% of the weight of the given mild surfactant.

A "high lathering surfactant" as defined herein, is one which lathers better than the long chain $C_{16}$–$C_{18}$ alkyl sulfate.

A "mild surfactant" as defined herein is one that is milder than sodium dodecyl sulfate.

Numerous examples of surfactants in general are disclosed in the patents incorporated herein by reference. They include limited amounts of anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chains for these other surfactants are $C_8$–$C_{22}$, preferably $C_{10}$–$C_{18}$. Alkyl glycosides and methyl glucose esters are preferred mild nonionics which may be mixed with other mild anionic or amphoteric surfactants in the compositions of this invention.

The bars of this invention can have up to about 10% of high lathering, non-mild surfactants and still maintain the mildness requirement of the bar. Examples of these surfactants include linear alkylbenzene sulfonates and shorter chain or traditional (coconut) alkyl sulfates.

A preferred syndet bar contains a mixture of $C_{12}$–$C_{14}$ alkyl isethionate (SCI) and sodium linear alkylbenzene sulfonate in a ratio of from about 35:1 to about 15:1, preferably from about 30:1 to about 30:1.

The primary basic binders of the present invention are: (1) free fatty acid and (2) paraffin wax.

The fatty acid material which is desirably incorporated into the present invention includes material ranging in hydrocarbon chain length of from abut 10 to about 22, essentially saturated. These fatty acids may be highly purified individual chain lengths and/or crude mixtures such as those derived from fats and oils.

The preferred ratio of stearic to lauric acids is dependent upon the level of mild synthetic surfactant(s), e.g., $C_{12}$–$C_{14}$ acyl isethionate, in the bar. Products that have higher levels of acyl isethionate require a larger ratio of stearic to lauric acid. The ratio is critical to the overall acceptability of a given product since it impacts product lather and smear, as well as processability. For high levels of acyl isethionate (>40%), the preferred ratio of stearic: lauric is from about 5:1 to about 10:1, more preferably from about 6:1 to about 9:1; moderate levels of acyl isethionate (between 45% and 30%), the preferred ratio of stearic:lauric is from about 2:1 to about 6:1, more preferably from about 3:1 to about 5:1; for low levels of acyl isethionate (<35%), the preferred ratio of stearic:lauric is from 0:1 (all stearic) to about 2:1, more preferably from 0:1 (all stearic) to about 0.5:1.

The composition may include soaps derived from hydrocarbon chain lengths of from about 10 to about 22, essentially saturated. It is preferred that the soap be the sodium salt, but other soluble soap can be used. Potassium, ammonium, triethanolammonium, and mixtures thereof, are deemed acceptable. The soaps are preferably prepared by the in situ saponification of the corresponding fatty acids, but they may also be introduced as preformed soaps.

"Insoluble" soaps, e.g., magnesium and zinc soaps, are not included in the 2–15% level of "soap" in the composition definition. However, insoluble soaps can be used as non-lathering, non-soil-load diluents.

An important component of this invention is a wax having a melting point (M.P.) of from about 130° F. to about 180° F. (54°–82° C.), preferably from about 140° F. to about 165° F. (60°–74° C.), and most preferably from about 142° F. to about 160° F. (61°–71° C.). A preferred paraffin wax is a fully refined petroleum wax which is odorless and tasteless and meets FDA requirements for use as coatings for food and food packages. Such paraffins are readily available commercially. A very suitable paraffin can be obtained, for example, from The National Wax Co. under the trade name 6975, The paraffin preferably is present in the bar in an amount ranging from about 4% to about 30% by weight. The paraffin ingredient is used in the product to impart skin mildness,, plasticity, firmness, and processability. It also provides a glossy look and smooth feet to the bar.

The paraffin ingredient is optionally supplemented by a microcrystalline wax. A suitable microcrystalline wax has a melting point ranging, for example, from about 140° F. (60° C.) to about 185° F. (85° C.), preferably from about 145° F. (62° C.) to about 175° F. (79° C.). The wax preferably should meet the FDA requirements for food grade microcrystalline waxes. A very suitable microcrystalline wax is obtained from Witco Chemical Company under the trade name Multiwax X-145A. The microcrystalline wax preferably is present in the bar in an amount ranging from about 0.5% to about 5% by weight. The microcrystalline wax ingredient imparts pliability to the bar at room temperatures.

Auxiliary plastic binders may be incorporated into the bar at levels of from 0% to about 10%. These binders may be selected from monoglycerides, polyethylene glycols, fatty alcohols, sugars, tallow alcohol ethoxylates, and mixtures thereof. Other plastic binders are identified in the published literature, such as J. Amer. Oil Chem. Soc. 1982, 59, 442. The binder system can contain several plasticizers.

The syndet bar of this invention may comprise 0% to about 5%, preferably from about 0.5% to about 3%, of a suitably fast hydrating cationic polymer. The polymers have molecular weights of from about 1000 to about 3,000,000.

The cationic polymer (skin conditioning agent) is selected from the group consisting of:
  (I) cationic polysaccharides;
  (II) cationic copolymers of saccharides and synthetic cationic monomers, and
  (III) synthetic polymers selected from the group consisting of:
    (A) cationic polyalkylene imines
    (B) cationic ethoxy polyalkylene imines, and
    (C) cationic poly[N-[-3-(dimethylammonio)-propyl]-N'-[3-(ethyleneoxyethylene dimethylammonio)propyl]urea dichloride].

Specific examples of members of the cationic polysaccharide class include the cationic hydroxyethyl cellulose JR 400 made by Union Carbide Corporation; the cationic starches Stalok ® 100, 200, 300 and 400 made by Staley, Inc.; the cationic galactomannans based on guar gum of the Galactasol 800 series by Henkel, Inc., and the Jaguar series by Celanese Corporation.

Examples of members of the class of copolymers of saccharides and synthetic cationic monomers include those composed of cellulose derivatives (e.g., hydroxyethyl cellulose) and N,N-diallyl,N-N-dialkyl ammonium chloride available from National Starch Corporation under the trade name Celquat.

The cationic synthetic polymers useful in the present invention are cationic polyalkylene imines, ethoxypolyalkylene imines, and poly[N-[-3-(dimethylammonio)propyl]-N'-[3-(ethyleneoxyethylene dimethylammonio)propyl]urea dichloride] the latter of which is available from Miranol Chemical Company, Inc., under the trademark of Miranol A-15, CAS Reg. No. 68555-36-2.

Preferred cationic polymeric skin conditioning agents of the present invention are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anhydroglucose unit to about 0.80 per anhydroglucose unit with the substituent cationic group being the adduct of 2,3-epoxypropyltrimethyl ammonium chloride to the natural polysaccharide backbone. Examples are JAGUAR C-14-S, C-15 and C-17 sold by Celanese Corporation. In order to achieve the benefits described in this invention, the polymer must have characteristics, either structural or physical which allow it to be suitably and fully hydrated and subsequently well incorporated into the soap matrix.

Other ingredients of the present invention are selected for the various applications. E.g., perfumes can be used in formulating the skin cleansing products, generally at a level of from about 0.1% to about 1.5% of the composition. Alcohols, hydrotropes, colorants, and fillers such as talc, clay, calcium carbonate and dextrin can also be used. Cetearyl alcohol is a mixture of cetyl and stearyl alcohols. Preservatives, e.g., sodium ethylenediaminetetraacetate (EDTA), generally at a level of less than 1% of the composition, can be incorporated in the cleansing products to prevent color and odor degradation. Anti-bacterials can also be incorporated, usually at levels up to 1.5%. Salts, both organic and inorganic, can be incorporated. Examples include sodium chloride, sodium isethionate, sodium sulfate, and their equivalents. The following patents disclose or refer to such ingredients and formulations which can be used in the soap/synbars of this invention, and are incorporated herein by reference:

| Pat. No. | Issue Date | Inventor(s) |
| --- | --- | --- |
| 4,234,464 | 11/1980 | Morshauser |
| 4,061,602 | 12/1977 | Oberstar et al. |
| 4,472,297 | 9/1984 | Bolich et al. |
| 4,491,539 | 1/1985 | Hoskins et al. |
| 4,540,507 | 9/1985 | Grollier |
| 4,673,525 | 6/1987 | Small et al. |
| 4,704,224 | 11/1987 | Saud |
| 4,812,253 | 3/1989 | Small et al. |
| 4,820,447 | 4/1989 | Medcalf et al. |
| 4,954,282 | 9/1990 | Rys et al. |

The syndet bars of this invention have a pH of from 4 to 9 in a 1% aqueous solution. The preferred pH is from 5 to 8, more preferably about 6.5 to 7.5.

Laboratory Assessment of Bar

The following test procedures are used to evaluate the critical bar performance attributes of mildness and bar processability.

Smear Test Procedure

Equipment:
1. #2-202C Fisher Brand Hexagonal Polystyrene weighing dishes (4"×3").
2. #14-366A Fisher Brand Spatula.
3. Balance capable of weighing to two decimal points.
4. 120° F. temperature Room.
5. Timer.

Test Method

The bar is placed in 30 mls of 100° F. (~38° C.) water for two hours. The wet surface is scraped and the weight of this material is called the "wet" smear grade. The wet smear is dried, as is the liquid soak material, the weights of these combined is the "dry" smear grade.

Bar Soap Handwash Lather Volume Test

The handwash lather test is used to provide in-use lather volume measurements for the lather performance of skin cleansing bars. The test measures both the ultimate lather volume generated and the volume which is generated after a very short lathering period (to reflect lathering ease). The lather volumes are generated under soil-loaded conditions.

Synthetic soil is used for the soil-loaded lather volume test reported herein. Its formula and procedure for making it are set out below.

TABLE 1

| Synthetic Soil | |
|---|---|
| Ingredients | Wt. % |
| Hyfac 430[a] | 1.87 |
| Lauric Acid[b] | 1.42 |
| Neo-fat 14[c] | 5.68 |
| Neo-fat 16[d] | 11.16 |
| Neo-fat 18[e] | 5.40 |
| Neo-fat 90-04[f] | 9.81 |
| Industrene 226[g] | 1.26 |
| Paraffin Wax | 7.30 |
| Squalane[h] | 3.70 |
| Lanolin Anhydrous | 19.40 |
| Coconut Oil | 3.30 |
| Tallow | 29.70 |
| | 100.00% |

[a]Emery Industries, Inc., Cincinnati, Ohio
[b]Emery Industries, Inc., Cincinnati, Ohio
[c]Armour Industrial Chemical Co., Chicago, Illinois
[d]Armour Industrial Chemical Co., Chicago, Illinois
[e]Armour Industrial Chemical Co., Chicago, Illinois
[f]Armour Industrial Chemical Co., Chicago, Illinois
[g]Humko Products, Memphis, Tennessee
[h]Robeco Chemicals, Inc., New York, New York Procedure
1. Heat above materials together continuously between 160°-175° F.
2. Mix 25 parts of above formula with 25 parts of a 5% to 80% tallow/20% coconut soap solution and 50 parts of distilled water at 150° F.
3. Cool mixture to room temperature while stirring constantly.
4. Store in covered glass container.

Equipment
The following equipment is used:
1. Water source and sink with temperature control. The water source should be medium hardness (6-9 grain/gallon) for most testing, although water of lower and higher hardness can be used for special purposes.
2. Synthetic soil (see Table 1).
3. Paper towels.
4. Test bars.
5. Control bars.

Procedure
The following procedure is used:
1. Set temperature at 95°-100° F.
2. Rub 0.22 cc of soil on hands.
3. Wet hands.
4. Rotate bar 3 times in both hands.
5. Add a little water, rub both hands 5 times.
6. Rotate hands 3 times (without soap), grade for flash volume.
7. Rotate 7 more times, grade for ultimate volume.
8. Collect lather and deposit on sink top.
9. Compare volume with standard bar target volume and assign grade.

Grading Scale

Soil Loaded

7—Exceptional
6—Very much higher than target
5—Higher than target
4—Target volume
3—Slightly lower than target
2—Lower than target In Vitro Skin Barrier Penetration Test (Mildness)

This test was performed according to the procedure described in U.S. Pat. No. 4,812,253, Small et al., issued Mar. 14, 1989, said patent incorporated herein by reference.

Frequently, materials which tends to improve processability also tend to have other negatives, particularly in terms of product mildness. Referring to Table 2, using the barrier destruction method to assess product mildness, individual raw materials sodium cetearyl sulfate is shown to be surprisingly more mild than the ultra mild sodium cocoglycerylether sulfonate, as well as a shorter chained AS, sodium dodecyl sulfate. The lower the number in Table 2 the milder the product.

TABLE 2

| | Mg $^3H_2O$ Transported |
|---|---|
| Water | 0.137 |
| Sodium Cetearyl Sulfate | 0.302 |
| Sodium Cocoglycerylether Sulfonate | 0.458 |
| Sodium Dodecyl Sulfate | 1.289 |
| Sodium Laurate | 1.805 |

Assessment of Processability: The Mill Test

Mill Test Procedure
1. A standard three-roll mill is employed with the take-up roll set at 120° F. (48° C.), the transfer roll at 110° F. (43° C.) and the discharge roll at 80° F. (26° C.).
2. Final flake thickness is about 0.010 inches.
3. After the third mill pass, the material is evaluated as described below.

Assessment

| Grade | Product Appearance |
|---|---|
| 10 | Soap-like. |
| 9 | Non-sticky; less than four compaction layers; no build-up. |
| 8 | Non-sticky; less than four compaction layers; 0.010" build-up. |
| 7 | Slightly sticky; about eight compaction layers; 0.010"–0.016" build-up. |
| 6 | Slightly sticky; large chunks; bridging; >0.016" build-up. |
| 5 | More sticky; sheeting; >0.016" build-up. |

Crutching
1. Add melted sodium cetearyl sulfate to the crutcher.
2. Add predetermined quantity of Hamposyl L-30 solution to the crutcher mix.
3. Add the predetermined quantity of AGS paste to the water in the crutcher. The AGS paste can be at ambient temperature or preheated to 150° F. (65° C.).
4. Turn on the agitator and recirculation pump and maintain temperature in crutcher at 130°-150° F. (54°-65° C.) by adjusting steam and water valves.
5. Allow contents in crutcher mix to return to 130°-150° F. (54°-65° C.) prior to adding predetermined quantity of stearic acid.
6. Add to heated crutcher mix predetermined quantity of soap or NaOH to form in-situ soap.
7. Allow the contents in the crutcher to mix and/or react for about 15 minutes while maintaining the temperature at 130°-150° F. (54°-65° C.).

8. Add sodium chloride plasticizer and titanium dioxide to the heated crutcher mix.
9. Add lauric and/or coconut fatty acids to crutcher mix and allow contents of crutcher to mix for about 15 minutes while maintaining temperature at 130°-150° F. (54°-65° C.).
10. Add paraffin wax in a molten form and allow crutcher to mix approximately ½ hour until uniform.

Drying

The crutcher mix is dried and cooled using a combination flash chamber and chill roll or chill belt. The crutcher mix is first heated to approximately 300° F. (149° C.) by a heat exchanger and then flash dried in a chamber above the chill roll or chill belt. From the flash chamber the hot, dried mix is extruded onto the chill roll or chill belt. The chill belt or chill roll provides a uniform, thin, cool (85°-95° F., 29°-35° C.) product in flake or chip form. Typical moisture for the flake is 1-10%, preferably about 2-4.5%. The ways to regulate the moisture, in the order of preference, are (1) increasing or decreasing steam pressure on the heat exchanger; (2) increasing or decreasing crutcher mix rate to the heat exchanger; and (3) increasing or decreasing crutcher mix temperature to the heat exchanger.

Amalgamating

The flakes are weighed and mixed in a batch amalgamator to obtain uniform flake size. Preweighed perfume is added to the flakes and mixed in the amalgamator to obtain the desired finished product perfume level. The perfumed flakes are transferred to the mix hopper or directly to the plodder.

Milling

The 3-roll soap mills are set up with the first roll at 120° F. (49° C.) and the other two mills at about 44° F. (7° C.). The material is passed through the mills several times to provide a homogeneous mixture of perfume and dried flakes.

Plodding and Stamping

The plodder is set up with the barrel temperature at about 115° F. (46° F.) and the nose temperature at 114°-122° F. (45°-50° C.). The ideal plodder is a dual stage plodder that allows use of a vacuum of about 15-25 inches (38-64 cm) of Hg. The plugs could be cut in 5-inch (13 cm) sections and stamped with a cold die block using die liquor such as alcohol, if appropriate.

EXAMPLES AND FORMULAS

The following formulas and examples are illustrative and are not intended to limit the scope of the invention(s). The methods of making milled bars are well known. All levels and ranges, temperatures, results etc., used herein are approximations unless otherwise specified. The bars of this invention in the Formulas and Examples all have a pH of about 6.5 to about 7.5.

The level of the water in the above syndet bars stabilizes upon storage from about 6% to about 3%.

COMPARATIVE BAR

Comparative Bar is DOVE ®, a currently marketed product based on sodium cocoyl isethionate. The ingredients of DOVE ® are: sodium cocoyl isethionate, stearic acid, sodium tallowate, water, sodium isethionate, coconut acid, sodium stearate, sodium dodecylbenzenesulfonate, sodium cocoate, fragrance, sodium chloride, and titanium dioxide. Performance properties show DOVE ® to be deficient in both lather, as well as smear, when compared with Examples 2 and 9 of the present invention. Since the exact composition of the product is not known, mill grade is not reported. Examples 1, and 3-8 have either improved smear or improved lather when compared with DOVE ®.

EXAMPLES 1-2

Examples 1 and 2 contain a high level of sodium cocoyl isethionate. In these cases, a relatively high ratio of stearic acid to lauric acid is required to achieve the correct balance of lather, smear and processability. The ratio must be carefully chosen, however. Example 1 demonstrates that when the stearic:lauric ratio gets too large (12.2:1), the soil lather becomes less desirable; notice that the smear is relatively poor as well. Example 2, with a somewhat lower stearic:lauric ratio (6.8:1 has improved soil lather and smear with no detriment to processability.

EXAMPLES 3-6

Examples 3 through 6 contain a moderate level of sodium cocoyl isethionate. This level of isethionate requires a lower stearic:lauric ratio than Examples 1 and 2, but, again, the ratio must be carefully chosen. As with Example 1, Example 3 has a stearic:lauric ratio (18.2:1) that is too high and results in poor lather performance. Example 4 has a stearic:lauric ratio that is too low (2:1) and the result is better lather but poor bar messiness, as well as decreased processability. Examples 5 and 6 have better balanced stearic:lauric ratios (4.1:1 and 5:1, respectively) and the result is the appropriate balance between lather, smear and processability.

EXAMPLES 7-9

Examples 7 through 9 represent products with lower levels of sodium cocoyl isethionate. As can be seen, all products contain substantially lower ratios of stearic:lauric acids. As Example 9 demonstrates, a well performing and processing product results when no stearic acid is added (ratio of stearic:lauric to zero).

Examples 2, 6 and 9 are highly preferred personal cleansing bars of the present invention which have very good lathers and smears with improved processability over bars of the current state of the art.

TABLE 3

| Ingredient | Comp. Bar (Wt. %) | Ex. 1 (Wt. %) | Ex. 2 (Wt. %) | Ex. 3 (Wt. %) |
|---|---|---|---|---|
| Sodium Cocoyl Isethionate | * | 51.80 | 50.90 | 40.60 |
| Sodium Linear Alkylbenzene Sulfonate | * | 2.00 | 1.90 | 1.60 |
| Sodium Cetearyl Sulfate | * | — | 11.20 | 11.20 |
| Paraffin | * | 9.90 | 9.70 | 9.70 |
| Sodium Soap (in situ) | * | 8.30 | 4.60 | 9.30 |
| Lauric Acid | * | 1.20 | 1.20 | 0.90 |
| Stearic Acid | * | 14.60 | 8.20 | 16.40 |
| Sodium Chloride | * | 0.50 | 0.50 | 0.01 |
| Sodium Isethionate | * | 5.90 | 5.80 | 4.60 |
| Titanium Dioxide | * | 0.25 | 0.25 | 0.25 |
| Perfume | * | 1.20 | 1.20 | 1.20 |
| Water | * | 4.50 | 4.50 | 4.50 |
| Ratio of Stearic: |  |  |  |  |
| Lauric Acids | * | 12.2:1 | 6.8:1 | 18.2:1 |
| Performance Data: |  |  |  |  |
| Avg. Soil Lather | 3.0 | 2.75 | 3.75 | 1.25 |
| Smear, Wet | 3.8 | 4.5 | 2.4 | 2.5 |
| Smear, Dry | 1.6 | 2.7 | 1.7 | 1.5 |
| Processability |  |  |  |  |

TABLE 3-continued

| Ingredient | Comp. Bar (Wt. %) | Ex. 1 (Wt. %) | Ex. 2 (Wt. %) | Ex. 3 (Wt. %) |
|---|---|---|---|---|
| Mill Grade | — | 9.00 | 9.00 | 9.00 |

*Not known.

Example 2 has a mill grade of 9 which is as good as an all-soap bar. Example 2 has a superior Average Soil Lather of 3.75 vs. 3.0 for the Comparative Bar. Example 2 has a superior wet smear of 2.4 vs. 3.8 for the Comparative Bar. Example 2 has a Dry Smear of 1.7 which is comparable to the 1.6 Dry Smear of the Comparative Bar.

TABLE 4

| Ingredient | Ex. 4 (Wt. %) | Ex. 5 (Wt. %) | Ex. 6 (Wt. %) |
|---|---|---|---|
| Sodium Cocoyl Isethionate | 40.60 | 40.60 | 39.00 |
| Sodium Linear Alkylbenzene Sulfonate | 1.60 | 1.60 | 1.60 |
| Sodium Cetearyl Sulfate | 11.20 | 11.20 | 9.53 |
| Paraffin | 9.70 | 9.70 | 14.10 |
| Sodium Soap (in situ) | 9.30 | 9.30 | 8.90 |
| Lauric Acid | 5.80 | 3.40 | 2.80 |
| Stearic Acid | 11.60 | 14.00 | 13.90 |
| Sodium Chloride | 0.01 | 0.01 | 0.01 |
| Sodium Isethionate | 4.60 | 4.60 | 4.50 |
| Titanium Dioxide | 0.25 | 0.25 | 0.25 |
| Perfume | 1.20 | 1.20 | 1.20 |
| Water | 4.50 | 4.50 | 4.50 |
| Ratio of Stearic:Lauric Acids | 2:1 | 4.1:1 | 5:1 |
| Performance Data: | | | |
| Avg. Soil Lather | 4.25 | 3.75 | 2.75 |
| Smear, Wet | 4.3 | 3.5 | 2.3 |
| Smear, Dry | 2.3 | 1.9 | 1.3 |
| Processability | | | |
| Mill Grade | 7.50 | 8.00 | 9.00 |

TABLE 5

| Ingredient | Ex. 7 (Wt. %) | Ex. 8 (Wt. %) | Ex. 9 (Wt. %) |
|---|---|---|---|
| Sodium Cocoyl Isethionate | 31.10 | 31.10 | 33.20 |
| Sodium Lauroyl Sarcosinate | 5.90 | 5.90 | 5.90 |
| Sodium Cetearyl Sulfate | 15.73 | 15.73 | 27.99 |
| Paraffin | 27.60 | 27.60 | 16.40 |
| Sodium Soap (in situ) | 3.00 | 3.00 | 3.00 |
| Lauric Acid | 4.60 | 1.60 | 4.40 |
| Stearic Acid | — | 3.00 | — |
| Sodium Chloride | 0.80 | 0.80 | 0.80 |
| Sodium Sulfate | 0.89 | 0.89 | 0.42 |
| Sodium Isethionate | 4.70 | 4.70 | 4.60 |
| Titanium Dioxide | 0.25 | 0.25 | 0.25 |
| Perfume | 1.20 | 1.20 | 1.20 |
| Water | 4.50 | 4.50 | 4.50 |
| Ratio of Stearic:Lauric Acids | 0:1 | 1.9:1 | 0:1 |
| Performance Data: | | | |
| Avg. Soil Lather | 3.75 | 1.50 | 3.00 |
| Smear, Wet | 2.5 | 2.8 | 3.4 |
| Smear, Dry | 2.0 | 1.8 | 2.3 |
| Processability | | | |
| Mill Grade | 7.50 | 6.50 | 8.00 |

Referring to the Performance Data in Tables 3 and 5, note that Example 9 has a good Mill Grade of 8. Example 9 has comparable lather vs. that of the Comparative Bar. Example 9 has a Wet Smear that is better, but its Dry Smear is slightly worse than that of the Comparative Bar.

What is claimed is:

1. A personal cleansing bar comprising:
   A. from about 4% to about 32% of essentially saturated long chain ($C_{15}$–$C_{22}$) synthetic surfactant selected from the group consisting of: alkyl sulfate, alkyl sarcosinate, alkyl glyceryl ether sulfonate, and mixtures thereof;
   B. from about 4% to about 30% of paraffin wax having a melting point of from about 130° F./54° C. to about 180° F./82° C;
   C. from about 20% to about 70% lathering mild synthetic surfactant selected from $C_{12}$–$C_{14}$ acyl isethionate, $C_{12}$–$C_{14}$ alkyl glyceryl ether sulfonate, $C_{12}$–$C_{14}$ sodium acyl sarcosinate, and mixtures thereof; and wherein at least about 10% of said bar is said mild lathering $C_{12}$–$C_{14}$ alkyl isethionate;
   D. from about 2% to about 30% free fatty acid; wherein said fatty acid is selected from the group consisting of stearic and lauric acids; said stearic and lauric acids having a ratio of from about 0:1 to about 2:1, and mixtures thereof;
   E. from about 2% to about 15% soap;
   F. from about 2% to about 8% sodium isethionate;
   G. from 0% to about 2% sodium chloride;
   H. from about 1.5% to about 10% water; and
   wherein said bar has a pH of from about 4.0 to about 9.0.

2. The bar of claim 1 wherein said wax has a melting point of from about 140° F./60° C. to about 165° F./74° C. and said lathering mild surfactant is said $C_{12}$–$C_{14}$ acyl isethionate.

3. The bar of claim 1 wherein said bar contains from about 3% to about 20% of said free fatty acid.

4. The bar of claim 1 wherein said wax melting point is from about 142° F./61° C. to about 160° F./71° C., and said pH is from about 6.5 to about 7.5; and wherein said bar contains from about 2% to about 8% water; from about 3% to about 7% sodium isethionate; and from about 0.01% to about 1.5% sodium chloride.

5. The personal cleansing bar of claim 1 wherein said bar has: from about 5% to about 30% of said saturated long chain ($C_{16}$–$C_{18}$) alkyl sulfates; from about 2% to about 10% of said soap; from about 40% to about 60% of said lathering mild surfactant selected from $C_{12}$–$C_{14}$ alkyl isethionate, sodium lauroyl sarcosinate, and $C_{12}$–$C_{14}$ alkyl glyceryl sulfonates, and mixtures thereof; from about 5% to about 28% of said paraffin wax having a melting point of from about 140° F./60° C. to about 165° F./74° C.; and from about 2% to about 8 water; said stearic ($C_{16}$–$C_{18}$) and said lauric ($C_{12}$) free fatty acids being present at a level of from about 3% to about 20%; and wherein said bar has a pH of from about 5.0 to about 8.

6. The bar of claim 1 wherein said bar contains from about 3% to about 20% of said free fatty acid and said long chain synthetic surfactant includes from about 3% to about 20% $C_{16}$–$C_{18}$ acyl isethionate by weight of said bar.

7. A personal cleansing bar comprising:
   A. from about 4% to about 32% of essentially saturated long chain ($C_{15}$–$C_{22}$) synthetic surfactant selected from the group consisting of: alkyl sulfate, alkyl sarcosinate, alkyl glyceryl ether sulfonate, and mixtures thereof;
   B. from about 4% to about 30% of paraffin wax having a melting point of from about 130° F./54° C. to about 180° F./82° C;
   C. from about 40% to about 70% lathering mild synthetic surfactant selected from $C_{12}$–$C_{14}$ acyl isethionate, $C_{12}$–$C_{14}$ alkyl glyceryl ether sulfonate, $C_{12}$–$C_{14}$ sodium acyl sarcosinate, and mixtures thereof; and wherein at least about 10% of said bar is said mild lathering $C_{12}$-$C_{14}$ alkyl isethionate;

D. from about 2% to about 30% stearic and lauric free fatty acids having a ratio of from about 5:1 to about 10:1, and mixtures thereof;

E. from about 2% to about 15% soap;

F. from about 2% to about 8% sodium isethionate;

G. from 0% to about 2% sodium chloride;

H. from about 1.5% to about 10% water; and wherein said bar has a pH of from about 4.0 to about 9.0.

8. The bar of claim 7 wherein said wax has a melting point of from about 140° F./60° C. to about 165° F./74° C. and said lathering mild surfactant is said $C_{12}$-$C_{14}$ acyl isethionate.

9. The bar of claim 7 wherein said bar contains from about 3% to about 20% of said free fatty acid.

10. A personal cleansing bar comprising:

A. from about 4% to about 32% of essentially saturated long chain ($C_{15}$-$C_{22}$) synthetic surfactant selected from the group consisting of: alkyl sulfate, alkyl sarcosinate, alkyl glyceryl ether sulfonate, and mixtures thereof;

B. from about 4% to about 30% of paraffin wax having a melting point of from about 130° F./54° C. to about 180° F./82° C;

C. from about 30% to about 45% lathering mild synthetic surfactant selected from $C_{12}$-$C_{14}$ acyl isethionate, $C_{12}$-$C_{14}$ alkyl glyceryl ether sulfonate, $C_{12}$-$C_{14}$ sodium acyl sarcosinate, and mixtures thereof; and wherein at least about 10% of said bar is said mild lathering $C_{12}$-$C_{14}$ alkyl isethionate;

D. from about 2% to about 30% of a mixture of stearic and lauric free fatty acids having a ratio of from about 2:1 to about 6:1, and mixtures thereof;

E. from about 2% to about 15% soap;

F. from about 2% to about 8% sodium isethionate;

G. from 0% to about 2% sodium chloride;

H. from about 1.5% to about 10% water; and wherein said bar has a pH of from about 4.0 to about 9.0.

11. The bar of claim 10 wherein said wax has a melting point of from about 140° F./60° C. to about 165° F./74° C. and said lathering mild synthetic surfactant is said $C_{12}$-$C_{14}$ acyl isethionate.

12. The bar of claim 11 wherein said bar contains from about 3% to about 20% of said free fatty acid.

13. The bar of claim 10 wherein said bar contains from about 3% to about 20% of said free fatty acid and said long chain synthetic surfactant includes from about 3% to about 20% $C_{16}$-$C_{18}$ acyl isethionate by weight of said bar.

* * * * *